(12) United States Patent
Shu et al.

(10) Patent No.: US 12,315,602 B1
(45) Date of Patent: May 27, 2025

(54) PORTABLE EXPERIMENTAL DEVICE FOR HAZARDOUS CHEMICAL AND EXPERIMENTAL METHOD THEREOF

(71) Applicant: INSTITUTE OF URBAN SAFETY AND ENVIRONMENTAL SCIENCE, BEIJING ACADEMY OF SCIENCE AND TECHNOLOGY, Beijing (CN)

(72) Inventors: Mushui Shu, Beijing (CN); Xiaohui Ji, Beijing (CN); Yu Wang, Beijing (CN); Wei Yao, Beijing (CN); Baoqian Dai, Beijing (CN); Ding Ding, Beijing (CN); Zhizhen Xu, Beijing (CN); Yan Dou, Beijing (CN); Ling Guo, Beijing (CN); Pengyao Zhou, Beijing (CN); Haijiao Li, Beijing (CN); Shuo Xiang, Beijing (CN); Na Zhang, Beijing (CN); Jianhua Guo, Beijing (CN)

(73) Assignee: Institute Of Urban Safety and Environmental Science, Beijing Academy of Science and Technology, Beijing (CN)

( * ) Notice: Subject to any disclaimer, the term of this patent is extended or adjusted under 35 U.S.C. 154(b) by 0 days.

(21) Appl. No.: 19/048,847

(22) Filed: Feb. 7, 2025

(30) Foreign Application Priority Data

May 13, 2024 (CN) .......................... 202410586346.8

(51) Int. Cl.
*G16C 20/10* (2019.01)
*B01L 1/00* (2006.01)
*G16C 20/70* (2019.01)

(52) U.S. Cl.
CPC ................ *G16C 20/10* (2019.02); *B01L 1/52* (2019.08); *G16C 20/70* (2019.02)

(58) Field of Classification Search
CPC ........... G16C 20/10; G16C 20/70; B01L 1/52; G06N 10/00; G06N 10/70
See application file for complete search history.

(56) References Cited

U.S. PATENT DOCUMENTS

2015/0100248 A1    4/2015   Daulton et al.

FOREIGN PATENT DOCUMENTS

| CN | 201600311 U | 10/2010 |
| CN | 101413862 B | * 12/2010 |

(Continued)

OTHER PUBLICATIONS

N. Liberatore et al, Compact GC-QEPAS for On-Site Analysis of Chemical Threats,Journal, Jan. 31, 2023, vol. 23, issue. 01, Sensors, Swiss.

*Primary Examiner* — Lam S Nguyen
(74) *Attorney, Agent, or Firm* — Ming Jiang; OPENPTO US LLC

(57) ABSTRACT

The disclosure relates to the technical field of experimental detection. A portable experimental device for hazardous chemical and an experimental method thereof are provided. The technical scheme of the disclosure integrates hazardous chemicals information and data of a portable meeting-water air release test device data to construct a perfect hazardous chemicals database, and realizes rapid prediction and response to a fire scene through scene data collection, preprocessing and matching. The scene data of the portable device is received and processed, and is compared with the database information, the random forest model is used to train the chemical reaction prediction model, and the real-time detection data is predicted to obtain the second prediction result. and the test experimental results are shared to each mobile terminal in time to realize the rapid transmission and sharing of information.

6 Claims, 6 Drawing Sheets

(56) References Cited

FOREIGN PATENT DOCUMENTS

| | | | | |
|---|---|---|---|---|
| CN | 102109448 | A | 6/2011 | |
| CN | 202204750 | U * | 4/2012 | |
| CN | 111781090 | A * | 10/2020 | ............... G01N 7/18 |
| CN | 115099673 | A | 9/2022 | |
| KR | 20210017868 | A | 2/2021 | |

* cited by examiner

```
┌─────────────────────────────────────────────────────────────┐
│ obtain hazardous chemicals information and portable experimental device │
│ basic information for hazardous chemicals, where the hazardous │
│ chemicals information includes chemical name and chemical formula │
│ information, physical property information, chemical property │
│ information and hazardous characteristic information, and the portable │
│ experimental device basic information for hazardous chemicals includes │
│ sensor information, location information, device operation information │
│ and network information, and build a hazardous chemicals database │
│ based on obtained hazardous chemicals information and portable │
│ experimental device basic information for hazardous chemicals │
└─────────────────────────────────────────────────────────────┘ — S101
                             │
┌─────────────────────────────────────────────────────────────┐
│ receive scene detection data collected by the portable experimental │
│ device for hazardous chemicals in a fire scene, match the scene │
│ detection data after preprocessing with information in the hazardous │
│ chemicals database, so as to a first fire scene prediction result │
└─────────────────────────────────────────────────────────────┘ — S102
                             │
┌─────────────────────────────────────────────────────────────┐
│ divide scene detection data preprocessed data into a training set and a test set, │
│ and train a random forest model by using the training set according to a │
│ relationship between hazardous chemical fire risks and characteristics, so as to │
│ obtain a fire scene chemical reaction prediction model │
└─────────────────────────────────────────────────────────────┘ — S103
                             │
┌─────────────────────────────────────────────────────────────┐
│ substitute scene detection data obtained by real-time detection of │
│ the portable experimental device for hazardous chemicals in a fire │
│ scene into the fire scene chemical reaction prediction model, so as to │
│ obtain a second fire scene prediction result │
└─────────────────────────────────────────────────────────────┘ — S104
                             │
┌─────────────────────────────────────────────────────────────┐
│ compare the first fire scene prediction result with the second fire scene │
│ prediction result, where if a comparison result is consistent, a fire scene test │
│ experimental result is generated, and share the fire scene test experimental result │
│ to each mobile terminal device at a fire scene │
└─────────────────────────────────────────────────────────────┘ — S105
```

FIG. 1

PORTABLE EXPERIMENTAL DEVICE FOR HAZARDOUS CHEMICAL AND EXPERIMENTAL METHOD THEREOF

CROSS-REFERENCE TO RELATED APPLICATIONS

This application claims priority of Chinese Patent Application No. 202410586346.8, filed on May 13, 2024, the content of which is hereby incorporated by reference.

TECHNICAL FIELD

The disclosure relates to the technical field of experimental detection, in particular to a portable experimental device for hazardous chemical and experimental method thereof.

BACKGROUND

The storage and improper use of hazardous chemicals can easily lead to fire accidents, and the on-site treatment of such accidents has always been a major challenge for fire emergency. At present, the fire extinguishing medium mainly used by the fire department in fire disposal is water. However, for some hazardous chemicals, a series of chemical reactions may occur after contact with water, resulting in combustible gas, oxygen or toxic gas. In this case, using water to put out the fire can not only fail to achieve the expected effect, but may aggravate the seriousness of the hazard.

When dealing with fires involving dangerous chemicals, there are the following difficulties.

Difficulty in obtaining information: at the scene of an accident, information such as the types, properties and possible reactions of dangerous chemicals is very important. However, due to the lack of digital means, this information may be difficult to obtain in time and accurately, which leads to the problem of information asymmetry when rescuers deal with accidents.

Inaccurate reaction prediction: it is difficult for rescuers in a fire scene to predict the possible chemical reactions of hazardous chemicals when they meet with water and other media. This uncertainty increases the difficulty and risk of dealing with accidents.

Inefficient disposal: fire and emergency personnel may need longer time to assess the situation and make rescue plans, resulting in inefficient disposal of accidents.

Increased safety hazards: due to insufficient information, the use of inappropriate fire extinguishing media (such as water) may aggravate the hazards of accidents and even lead to secondary accidents, posing a greater threat to rescuers and the surrounding environment.

In order to provide and predict the information related to hazardous chemicals for firefighters and emergency personnel in a short time when dealing with fires involving hazardous chemicals, a portable experimental device for hazardous chemicals and experimental method thereof are developed.

SUMMARY

The purpose of the disclosure is to provide a portable experimental device for hazardous chemicals and an experimental method thereof, so as to solve the problem that when dealing with fires involving hazardous chemicals, firefighters and emergency personnel cannot know and predict the relevant information of hazardous chemicals in a short time due to insufficient information, which leads to have risks for firefighters and emergency personnel in fire fighting.

A portable experimental device for hazardous chemicals is provided, where the portable experimental device for hazardous chemicals includes an experimental device main body and a control device, the control device is installed inside the experimental device main body; an outer wall of the experimental device main body is provided with a display screen and buttons; a top of the experimental device main body is provided with a through hole for installing a water adding funnel, a funnel switch and a liquid-filled flask stopper; and a liquid-filled flask, a heating insulation electric jacket, a temperature sensor and a magnetic stirrer are further installed in the experimental device main body; the water adding funnel is installed on a top of the liquid-filled flask through the funnel switch, and a gas collection cabin is further installed inside the experimental device main body, and the gas collection cabin is connected with the liquid-filled flask through a connecting hose, and the gas collection cabin is provided with gas sensors, a movable scale and a laser transmitter and receiver; an inner wall of the experimental device main body is further provided with an explosion-proof battery and a liquid position monitoring device, and the liquid position monitoring device, the explosion-proof battery, the temperature sensor and the heating insulation electric jacket are electrically connected with the control device;

the control device includes a hazardous chemicals database construction unit, a first fire scene test experimental data analysis unit, a second fire scene test experimental data analysis unit and an information sharing unit;

the hazardous chemicals database construction unit, used for obtaining hazardous chemicals information and portable experimental device basic information for hazardous chemicals, where the hazardous chemicals information includes chemical name and chemical formula information, physical property information, chemical property information and hazardous characteristic information, and the portable experimental device basic information for hazardous chemicals includes sensor information, location information, device operation information and network information, and building a hazardous chemicals database based on obtained hazardous chemicals information and portable experimental device basic information for hazardous chemicals;

a first fire scene test experimental data analysis unit, used for receiving scene detection data collected by the portable experimental device for hazardous chemicals in a fire scene, matching the scene detection data after preprocessing with information in the hazardous chemicals database, so as to obtain a first fire scene prediction result;

a model optimization unit, used for dividing scene detection data preprocessed data into a training set and a test set, and training a random forest model by using the training set according to a relationship between hazardous chemical fire risks and characteristics, so as to obtain a fire scene chemical reaction prediction model;

the second fire scene test experimental data analysis unit, used for substituting scene detection data obtained by real-time detection of the portable experimental device for hazardous chemicals in a fire scene into the fire scene chemical reaction prediction model, so as to obtain a second fire scene prediction result;

the information sharing unit, used for comparing the first fire scene prediction result with the second fire scene prediction result, where if a comparison result is consistent, a fire scene test experimental result is generated, and the fire scene test experimental result is shared to each mobile terminal device at a fire scene.

In a second aspect, a portable experimental method for hazardous chemicals is provided, which is applied to the portable experimental device for hazardous chemicals, and includes:
  obtaining hazardous chemicals information and portable experimental device basic information for hazardous chemicals, where the hazardous chemicals information includes chemical name and chemical formula information, physical property information, chemical property information and hazardous characteristic information, and the portable experimental device basic information for hazardous chemicals includes sensor information, location information, device operation information and network information, and building a hazardous chemicals database based on obtained hazardous chemicals information and portable experimental device basic information for hazardous chemicals;
  receiving scene detection data collected by the portable experimental device for hazardous chemicals in a fire scene, matching the scene detection data after preprocessing with information in the hazardous chemicals database, so as to a first fire scene prediction result;
  dividing scene detection data preprocessed data into a training set and a test set, and training a random forest model by using the training set according to a relationship between hazardous chemical fire risks and characteristics, so as to obtain a fire scene chemical reaction prediction model;
  substituting scene detection data obtained by real-time detection of the portable experimental device for hazardous chemicals in a fire scene into the fire scene chemical reaction prediction model, so as to obtain a second fire scene prediction result;
  comparing the first fire scene prediction result with the second fire scene prediction result, where if a comparison result is consistent, a fire scene test experimental result is generated, and sharing the fire scene test experimental result to each mobile terminal device at a fire scene.

Further, the portable experimental method for hazardous chemicals is further includes:
  comparing the first fire scene prediction result with the second fire scene prediction result, where if a comparison result is inconsistent, various constraint conditions of fire scene working safety environment are set, and substituting scene detection data obtained by real-time detection of the portable experimental device for hazardous chemicals in a fire scene and information in the hazardous chemicals database into a preset genetic algorithm for genetic iteration, so as to obtain a third fire scene prediction result of various constraint conditions of the fire scene working safety environment.

Further, obtaining hazardous chemicals information and portable experimental device basic information for hazardous chemicals, the hazardous chemicals information including chemical name and chemical formula information, physical property information, chemical property information and hazardous characteristic information, and the portable experimental device basic information for hazardous chemicals including sensor information, location information, equipment operation information and network information, and building a hazardous chemicals database based on obtained hazardous chemicals information and portable experimental device basic information for hazardous chemicals includes:
  determining hazardous chemicals database data demand information, where the hazardous chemicals database data demand information includes hazardous chemicals information, information after reaction of hazardous chemicals with water and detection data of the portable experimental device for hazardous chemicals, and building a hazardous chemicals database data table according to the hazardous chemicals database data demand information;
  where the hazardous chemicals database data table includes a hazardous chemical table and an experimental device table, the hazardous chemical table includes fields such as chemical name, chemical formula, physical properties, chemical properties, hazardous characteristics, and the experimental device table includes fields such as sensor information, location information, device operation information, network information;
  using VARCHAR field for chemical symbols, and converting formula into a picture format by chemical formula and storing in a database, and building a chemical formula label for stored chemical formula;
  inputting real-time generated hazardous chemicals information and experimental device information into the database, and building a field index for query on the hazardous chemicals database.

Further, receiving scene detection data collected by the portable experimental device for hazardous chemicals in a fire scene, matching the scene detection data after preprocessing with information in the hazardous chemicals database to obtain a first fire scene prediction result includes:
  receiving real-time detection data collected from a fire scene by a portable experimental device for hazardous chemicals through wireless transmission or wired connection;
  building a fire scene information transmission network, where the fire scene information transmission network includes wireless transmission and wired connection, and the wireless transmission is preferentially used for transmitting scene detection data collected by a portable experimental device used for hazardous chemicals at a fire scene and information of each mobile terminal device at a fire scene;
  applying the portable experimental device for hazardous chemicals to a fire scene, and testing 100 g substances to be tested by the portable experimental device for hazardous chemicals, where substances to be tested include solid or liquid;
  collecting a liquid level height through a liquid position monitoring device by the portable experimental device for hazardous chemicals, judging reaction state by the control device according to data collected by the liquid position monitoring device, and transmitting information to an operator mobile terminal; where if the liquid level height meets a preset value, the funnel switch is started to add water through the water adding funnel and water pipe switch, and the funnel switch is closed until water completely covers object to be detected and a timer is started; when a preset time is reached, the magnetic stirrer starts stirring under an action of magnetic force, and the laser transmitter and receiver emits and receives once every 10 s after starting the timer, a moving distance of the movable scale is calculated according to received time, generated gas volume is calculated according to the moving distance and a cross-sectional area of the gas collection cabin, and a gas release speed is calculated according to generated gas volume and time, formed gas release speed time curve information is displayed on the display screen, and the gas release speed time curve information is transmitted to an operator control terminal;

after the timer is started, recording data once collected by the gas sensors every 10 s, and displaying formed concentration-time curve information on the display screen, and transmitting the gas release speed time curve information to the operator control terminal; reading and recording data after 15 min of reaction time, where volume test range is 25 ml-2000 ml; if the gas release speed time curve information and the concentration-time curve information fluctuate abnormally, a release gas rate exceeds L/min, and test is stopped in time and result is recorded as category A;

pre-processing test experiment detection result category A, and matching pre-processed test experiment detection result category A with information in the hazardous chemicals database to obtain the first fire scene prediction result, where the first fire scene prediction result includes hazardous characteristic information of test experiment detection result category A.

Further, the portable experimental method for hazardous chemicals further includes:

deploying trained fire scene chemical reaction prediction model to fire scene information transmission network application environment;

predicting real-time detected fire scene chemical reaction by the fire scene chemical reaction prediction model, and judging expected chemical reaction at a fire scene;

generating a portable experimental information report for hazardous chemicals, according to prediction results of the fire scene chemical reaction prediction model.

The disclosure has the following beneficial effects: the disclosure provides a portable experimental device for hazardous chemicals and an experimental method thereof. The technical scheme of the disclosure integrates hazardous chemicals information and data of a portable meeting-water air release test device data to construct a perfect hazardous chemicals database, and realizes rapid prediction and response to a fire scene through scene data collection, preprocessing and matching. By receiving and processing the scene data of the portable device and comparing it with the database information, the first prediction result is obtained. At the same time, the random forest model is used to train the chemical reaction prediction model, and the real-time detection data is predicted to obtain the second prediction result. Through the comparison of the two prediction results, the accuracy of the prediction is ensured, and the test experimental results are shared to each mobile terminal in time to realize the rapid transmission and sharing of information. This scheme combines database construction, scene data collection, model training and comparison of fire scene experimental detection results, which not only improves the accuracy of fire scene experimental detection, but also enhances the efficiency of emergency response in a scene, and provides strong technical support for fire scene experimental detection, prevention and rescue.

BRIEF DESCRIPTION OF THE DRAWINGS

In order to explain the technical scheme of the disclosure more clearly, the drawings needed to be used in the embodiment will be briefly introduced below. Obviously, for ordinary skilled in the field, other drawings can be obtained according to these drawings without making creative efforts.

FIG. 1 is a schematic flow chart of a portable experimental method for hazardous chemicals according to an embodiment of the disclosure;

Figure 2:
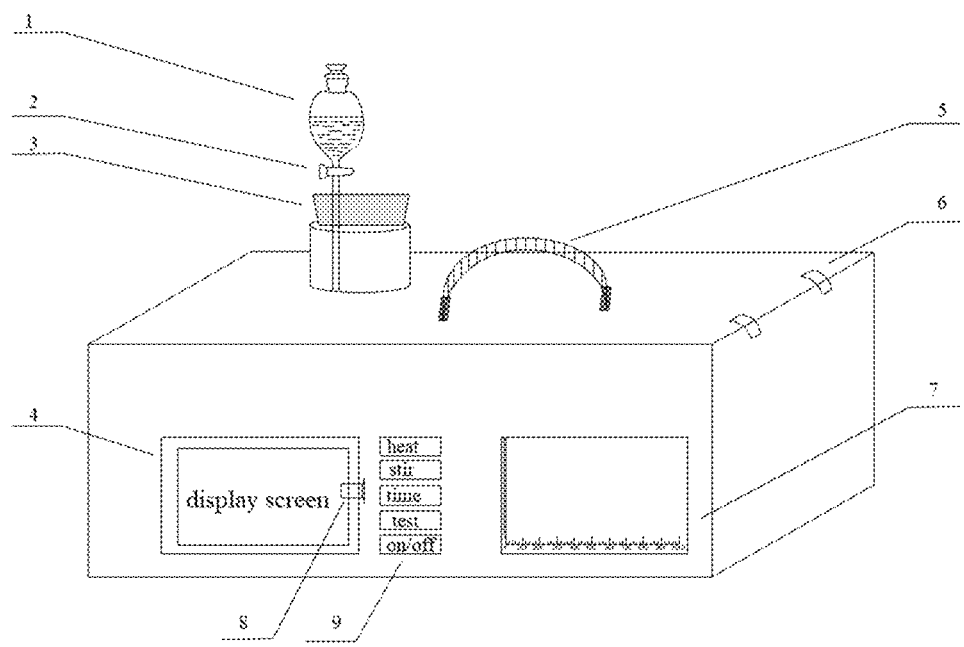
FIG. 2 is an overall front view according to an embodiment of the disclosure.
Figure 3:
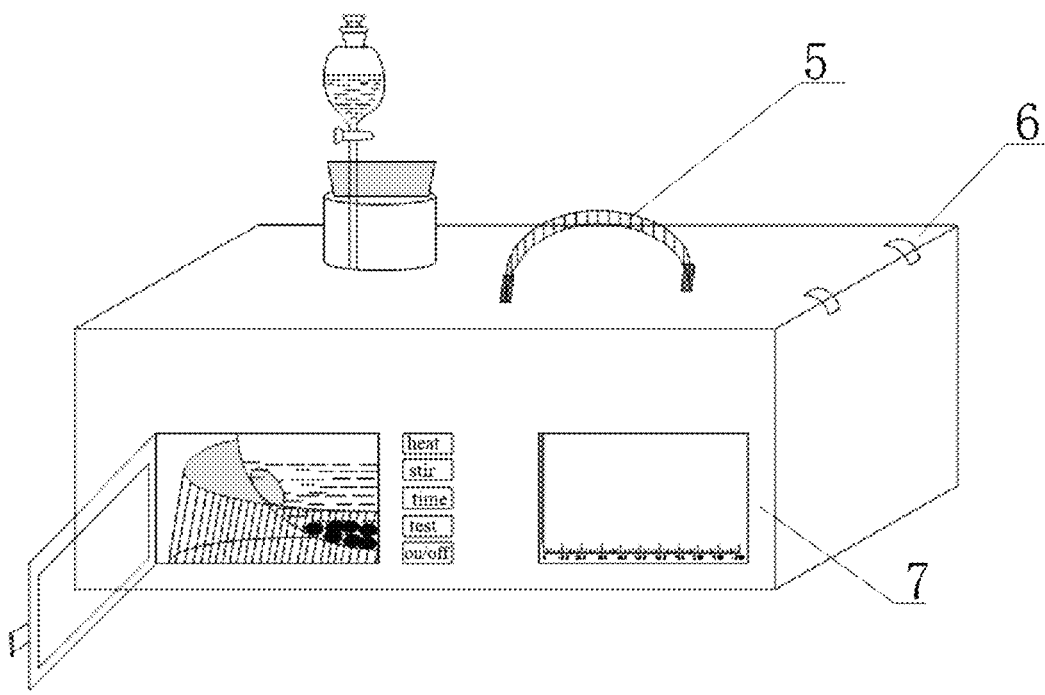
FIG. 3 is a schematic diagram for observing the liquid level height after the display screen is turned on according to an embodiment of the disclosure.
Figure 4:
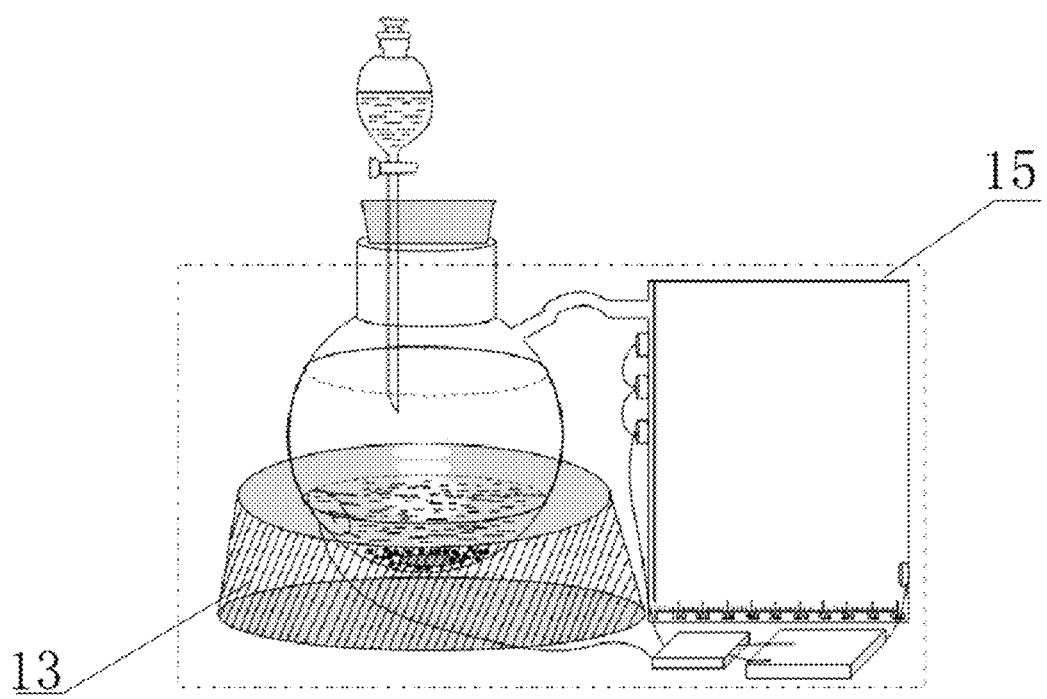
FIG. 4 is an internal view of the device in the initial state according to an embodiment of the disclosure.

List of reference characters: 1 water adding funnel; 2 funnel switch; 3 liquid-filled flask stopper; 4 display screen; 5 device handle; 6 top cover buckle; 7 flow window; 8 display screen buckle; 9 button; 10 liquid-filled flask; 11 heating insulation electric jacket; 12 temperature sensor; 13 magnetic stirrer; 14 connecting hose; 15 gas collection cabin; 16 gas sensor; 17 movable scale; 18 laser transmitter and receiver; 19 control device; and 20 explosion-proof battery.

DETAILED DESCRIPTION OF THE EMBODIMENTS

In order to make the purpose, technical scheme and advantages of the disclosure more clear, the technical scheme of the disclosure will be described clearly and completely with reference to specific embodiments of the disclosure and corresponding drawings. Obviously, the described embodiment is only a part of the embodiment of the disclosure, not all of the embodiment. Based on the embodiments in the disclosure, all other embodiments obtained by ordinary skilled in the field without creative efforts belong to the scope of protection of the disclosure. The technical scheme provided by each embodiment of the disclosure will be described in detail below with reference to the attached drawings.

The equipment end of the portable experimental device for hazardous chemicals transmits the collected data to the server end, and the server end processes the data and shares it with each mobile terminal device at the fire scene. Firefighters at the fire scene can know the predicted chemical hazard information, and the background control end is used to set the relevant requirements for data analysis and modify the background data. The portable experimental device for hazardous chemicals in the technical scheme of the disclosure includes a control device 19, and the control device 19 builds communication connection with sensors and electrical elements in the portable experimental device for hazardous chemicals in the disclosure for data transmission.

Compared with the meeting-water air release test experimental equipment with huge volume and long analysis period in the market, this device realizes rapid test and data analysis through the application of digital technology. The digital control system can efficiently process the experimental data, shorten the analysis period, and provide real-time test results, which is very suitable for the rapid response requirements of the accident site.

In the first aspect, a portable experimental device for hazardous chemicals is provided, the portable experimental device for hazardous chemicals includes an experimental device main body and a control device 19, the control device 19 is installed inside the experimental device main body; an outer wall of the experimental device main body is provided with a display screen 4 and buttons 9; a top of the experimental device main body is provided with a through hole for installing a water adding funnel 1, a funnel switch 2 and a liquid-filled flask stopper 3; and a liquid-filled flask 10, a heating insulation electric jacket 11, a temperature sensor 12 and a magnetic stirrer 13 are further installed in the experimental device main body; the water adding funnel 1 is installed on a top of the liquid-filled flask 10 through the funnel switch 2, and a gas collection cabin 15 is further installed inside the experimental device main body, and the gas collection cabin 15 is connected with the liquid-filled flask 10 through a connecting hose 14, and the gas collection cabin 15 is provided with gas sensors 16, a movable scale 17 and a laser transmitter and receiver 18; an inner wall of the experimental device main body is further provided with an explosion-proof battery 20 and a liquid position monitoring device, and the liquid position monitoring device, the explosion-proof battery 20, the temperature sensor 12 and the heating insulation electric jacket 11 are electrically connected with the control device 19.

The control device 19 includes a hazardous chemicals database construction unit, a first fire scene test experimental data analysis unit, a second fire scene test experimental data analysis unit and an information sharing unit.

The hazardous chemicals database construction unit, used for obtaining hazardous chemicals information and portable experimental device basic information for hazardous chemicals, where the hazardous chemicals information includes chemical name and chemical formula information, physical property information, chemical property information and hazardous characteristic information, and the portable experimental device basic information for hazardous chemicals includes sensor information, location information, device operation information and network information, and building a hazardous chemicals database based on obtained hazardous chemicals information and portable experimental device basic information for hazardous chemicals.

A first fire scene test experimental data analysis unit, used for receiving scene detection data collected by the portable experimental device for hazardous chemicals in a fire scene, matching the scene detection data after preprocessing with information in the hazardous chemicals database, so as to obtain a first fire scene prediction result.

A model optimization unit, used for dividing scene detection data preprocessed data into a training set and a test set, and training a random forest model by using the training set according to a relationship between hazardous chemical fire risks and characteristics, so as to obtain a fire scene chemical reaction prediction model.

The second fire scene test experimental data analysis unit, used for substituting scene detection data obtained by real-time detection of the portable experimental device for hazardous chemicals in a fire scene into the fire scene chemical reaction prediction model, so as to obtain a second fire scene prediction result.

The information sharing unit, used for comparing the first fire scene prediction result with the second fire scene prediction result, where if a comparison result is consistent, a fire scene test experimental result is generated, and the fire scene test experimental result is shared to each mobile terminal device at a fire scene.

The technical scheme of the disclosure further includes a computer device, which includes a memory and a processor, where the memory stores a computer program, and when the processor executes the computer program, the following steps are realized:

hazardous chemicals information and portable experimental device basic information for hazardous chemicals are obtained, where the hazardous chemicals information includes chemical name and chemical formula information, physical property information, chemical property information and hazardous characteristic information, and the portable experimental device basic information for hazardous chemicals includes sensor information, location information, device operation information and network information, and a hazardous chemicals database is built based on obtained hazardous chemicals information and portable experimental device basic information for hazardous chemicals;

scene detection data collected by the portable experimental device for hazardous chemicals in a fire scene is received, the scene detection data after preprocessing is matched with information in the hazardous chemicals database, so as to a first fire scene prediction result;

scene detection data preprocessed data is divided into a training set and a test set, and a random forest model is trained by using the training set according to a relationship between hazardous chemical fire risks and characteristics, so as to obtain a fire scene chemical reaction prediction model;

scene detection data obtained by real-time detection of the portable experimental device for hazardous chemicals in a fire scene is substituted into the fire scene chemical reaction prediction model, so as to obtain a second fire scene prediction result;

the first fire scene prediction result is compared with the second fire scene prediction result, where if a comparison result is consistent, a fire scene test experimental result is generated, and the fire scene test experimental result is shared to each mobile terminal device at a fire scene.

Based on the portable experimental device for hazardous chemicals, the meeting-water air release test experiment is performed through the digital technical scheme;

the portable experimental device for hazardous chemicals is applied to a fire scene, and 100 g substances to be tested is performed test experiment by the portable experimental device for hazardous chemicals, where substances to be tested include solid or liquid;

a liquid level height is collected through a liquid position monitoring device by the portable experimental device for hazardous chemicals, reaction state is judged by the control device 19 according to data collected by the liquid position monitoring device, and information is transmitted to an operator mobile terminal; where if the liquid level height meets a preset value, the funnel switch 2 is started to add water through the water adding funnel 1 and water pipe switch, and the funnel switch 2 is closed until water completely covers object to be detected and a timer is started; when a preset time is reached, the magnetic stirrer 13 starts stirring under an action of magnetic force, and the laser transmitter and receiver 18 emits and receives once every 10 s after starting the timer, a moving distance of the movable scale 17 is calculated according to received time, generated gas volume is calculated according to the moving distance and a cross-sectional area of the gas collection cabin 15, and a gas release speed is calculated according to generated gas volume and time, formed gas release speed time curve information is displayed on the display screen, and the gas release speed time curve information is transmitted to an operator control terminal;

after the timer is started, data is recorded once collected by the gas sensors 16 every 10 s, and formed concentration-time curve information is displayed on the display screen, and the gas release speed time curve information is transmitted to the operator control terminal; data is read and recorded after 15 min of reaction time, where volume test range is 25 ml-2000 ml; if the gas release speed time curve information and the concentration-time curve information fluctuate abnormally, a release gas rate exceeds L/min, and test is stopped in time and result is recorded as category A;

test experiment detection result category A is pre-processed, and pre-processed test experiment detection result category A is matched with information in the hazardous chemicals database to obtain the first fire scene prediction result, where the first fire scene prediction result includes hazardous characteristic information of test experiment detection result category A.

In the second aspect, as shown in FIG. 1, the disclosure provides a portable experimental method for hazardous chemicals, which is applied to the portable experimental device for hazardous chemicals, and includes the following steps.

In step S101, hazardous chemicals information and portable experimental device basic information for hazardous chemicals are obtained, where the hazardous chemicals information includes chemical name and chemical formula information, physical property information, chemical property information and hazardous characteristic information, and the portable experimental device basic information for hazardous chemicals includes sensor information, location information, device operation information and network information, and a hazardous chemicals database is built based on obtained hazardous chemicals information and portable experimental device basic information for hazardous chemicals.

In step S102, scene detection data collected by the portable experimental device for hazardous chemicals in a fire scene is received, the scene detection data after preprocessing is matched with information in the hazardous chemicals database, so as to a first fire scene prediction result.

In step S103, scene detection data preprocessed data is divided into a training set and a test set, and a random forest model is trained by using the training set according to a relationship between hazardous chemical fire risks and characteristics, so as to obtain a fire scene chemical reaction prediction model.

In step S104, scene detection data obtained by real-time detection of the portable experimental device for hazardous chemicals in a fire scene is substituted into the fire scene chemical reaction prediction model, so as to obtain a second fire scene prediction result.

In step S105, the first fire scene prediction result is compared with the second fire scene prediction result, where if a comparison result is consistent, a fire scene test experimental result is generated, and the fire scene test experimental result is shared to each mobile terminal device at a fire scene.

Specifically, the disclosure provides a portable experimental method for hazardous chemicals, which further includes the following steps.

The first fire scene prediction result is compared with the second fire scene prediction result, where if a comparison result is inconsistent, various constraint conditions of fire scene working safety environment are set, and scene detection data obtained by real-time detection of the portable experimental device for hazardous chemicals in a fire scene and information in the hazardous chemicals database are substituted into a preset genetic algorithm for genetic iteration, so as to obtain a third fire scene prediction result of various constraint conditions of the fire scene working safety environment.

Specifically, obtaining hazardous chemicals information and portable experimental device basic information for hazardous chemicals, the hazardous chemicals information including chemical name and chemical formula information, physical property information, chemical property information and hazardous characteristic information, and the portable experimental device basic information for hazardous chemicals including sensor information, location information, equipment operation information and network information, and building a hazardous chemicals database based on obtained hazardous chemicals information and portable experimental device basic information for hazardous chemicals includes the following steps:

hazardous chemicals database data demand information is determined, where the hazardous chemicals database data demand information includes hazardous chemicals information, information after reaction of hazardous chemicals with water and detection data of the portable experimental device for hazardous chemicals, and a hazardous chemicals database data table is built according to the hazardous chemicals database data demand information;

where the hazardous chemicals database data table includes a hazardous chemical table and an experimental device table, the hazardous chemical table includes fields such as chemical name, chemical formula, physical properties, chemical properties, hazardous characteristics, and the experimental device table includes fields such as sensor information, location information, network information, device operation information;

VARCHAR field is used for chemical symbols, and chemical formula converts formula into a picture format and stores in a database, and a chemical formula label is built for stored chemical formula;

real-time generated hazardous chemicals information and experimental device information is inputted into the database, and a field index is built for query on the hazardous chemicals database.

Specifically, receiving scene detection data collected by the portable experimental device for hazardous chemicals in a fire scene, matching the scene detection data after preprocessing with information in the hazardous chemicals database to obtain a first fire scene prediction result includes:

real-time detection data collected from a fire scene by a portable experimental device for hazardous chemicals is received through wireless transmission or wired connection.

Wireless network communication signal amplification devices are set at the fire scene, and the distance among each of wireless network communication signal amplification devices is 50 meters. In the wireless network communication signal amplification device in the area 100 meters away from the fire scene, network cable splitter device is added, network data is transmitted through wired network, and network communication base stations are installed at high altitude positions away from the fire scene for network data transmission.

A fire scene information transmission network is built, where the fire scene information transmission network includes wireless transmission and wired connection, and the wireless transmission is preferentially used for transmitting scene detection data collected by a portable experimental device used for hazardous chemicals at a fire scene and information of each mobile terminal device at a fire scene;

the portable experimental device for hazardous chemicals is applied to a fire scene, and test experiment is performed on 100 g substances to be tested by the portable experimental device for hazardous chemicals, where substances to be tested include solid or liquid;

a liquid level height is collected through a liquid position monitoring device by the portable experimental device for hazardous chemicals, reaction state is judged by the control device 19 according to data collected by the liquid position monitoring device, and information is transmitted to an operator mobile terminal; where if the liquid level height meets a preset value, the funnel switch 2 is started to add water through the water adding funnel 1 and water pipe switch, and the funnel switch 2 is closed until water completely covers object to be detected and a timer is started; when a preset time is reached, the magnetic stirrer 13 starts stirring under an action of magnetic force, and the laser transmitter and receiver 18 emits and receives once every 10 s after starting the timer, a moving distance of the movable scale 17 is calculated according to received time, generated gas volume is calculated according to the moving distance and a cross-sectional area of the gas collection cabin 15, and a gas release speed is calculated according to generated gas volume and time, formed gas release speed time curve information is displayed on the display screen, and the gas release speed time curve information is transmitted to an operator control terminal;

after the timer is started, data is recorded once collected by the gas sensors 16 every 10 s, and formed concentration-time curve information is displayed on the display screen, and the gas release speed time curve information is transmitted to the operator control terminal; data is read and recorded after 15 min of reaction time, where volume test range is 25 ml-2000 ml; if the gas release speed time curve information and the concentration-time curve information fluctuate abnormally, a release gas rate exceeds L/min, and test is stopped in time and result is recorded as category A;

test experiment detection result category A is pre-processed, and pre-processed test experiment detection result category A is matched with information in the hazardous chemicals database to obtain the first fire scene prediction result, where the first fire scene prediction result includes hazardous characteristic information of test experiment detection result category A.

Specifically, the disclosure provides a portable experimental method for hazardous chemicals, which further includes the following steps:

trained fire scene chemical reaction prediction model is deployed to fire scene information transmission network application environment;

real-time detected fire scene chemical reaction is predicted by the fire scene chemical reaction prediction model, and expected chemical reaction at a fire scene is judged;

a portable experimental information report for hazardous chemicals is generated according to prediction results of the fire scene chemical reaction prediction model.

Referring to FIGS. 2 to 6, the disclosure provides a portable experimental device for hazardous chemicals, and the technical scheme of the disclosure can also be used to manually perform the meeting-water air release test experiment.

Figure 5:
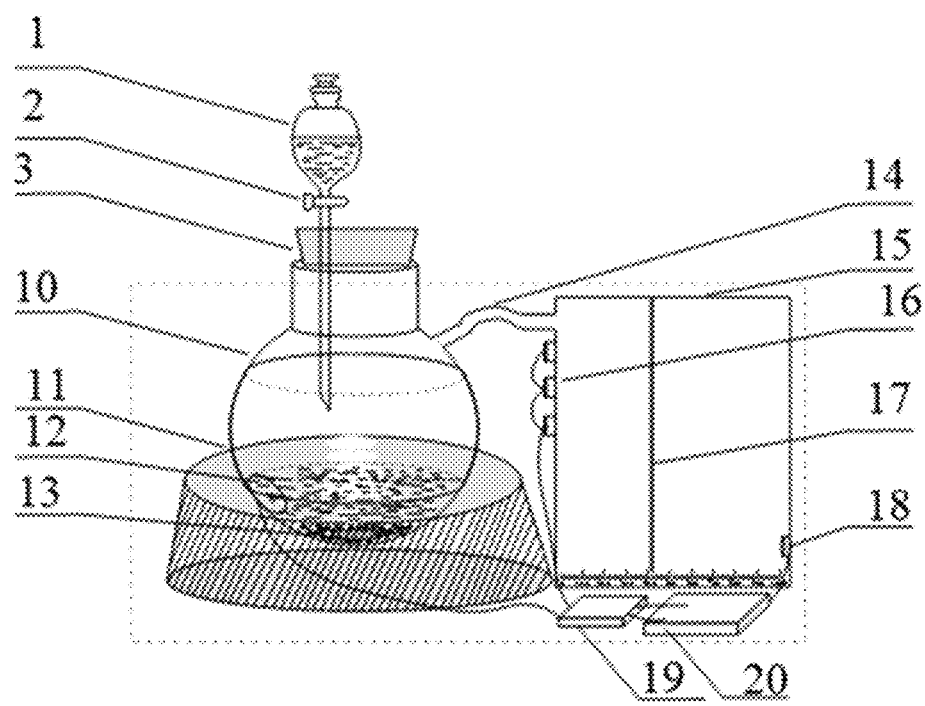
FIG. 5 is an internal view of the device in the state of reaction process according to an embodiment of the disclosure.
Figure 6:
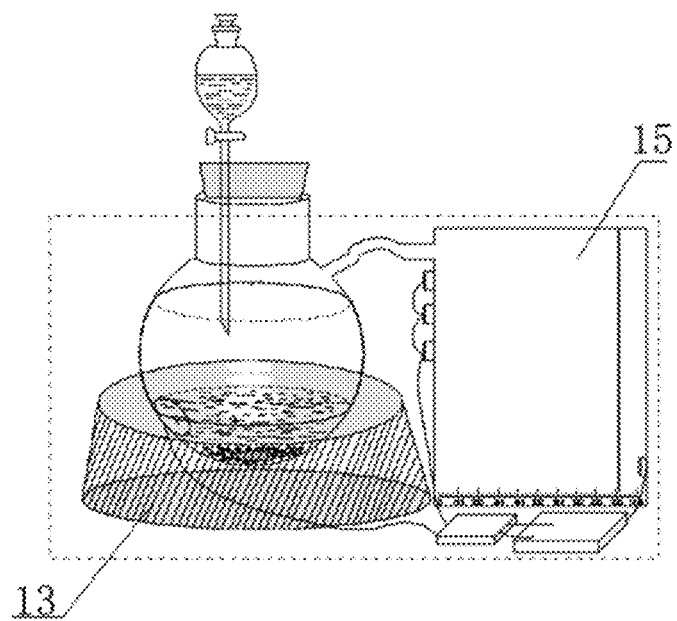
FIG. 6 is an internal view of the device in a state where the reaction is finished according to an embodiment of the disclosure.

The front view of the device is shown in FIG. 2, and the inside view of the device is shown in FIG. 5. The device mainly includes a water adding funnel 1, a liquid-filled flask 10, a heating insulation electric jacket 11, a gas collection cabin 15, gas sensors 16, a laser transmitter and receiver 18, a control device 19, a display screen 4 and buttons 9, a liquid position monitoring device and an explosion-proof battery 20.

As can be seen from the above embodiments, a portable experimental device for hazardous chemicals provided by the disclosure. Where, the connection between the water adding funnel 1 and the liquid-filled flask stopper 3, and the connection between the liquid-filled flask stopper 3 and the liquid-filled flask 10 are a hard and rubber plug connection, which requires good sealing performance. There is a gas volume scale on the flow windows 7, which is convenient for reading the volume when the laser calculation volume fails on site. The connecting hose 14 and the gas collection cabin 15 are directly connected by soft materials such as rubber hose and silicone hose, and the sealing is good. The temperature sensor 12 is attached to the outer wall of the liquid-filled flask 10 to test the heating situation of the flask during the reaction, so as to calculate the reaction heat. The gas sensors 16 and the gas collection cabin 15 are sealed by adhesive, which has good sealing performance. The laser transmitter and receiver 18 is a flat mirror with a reflective surface on the right side for reflecting laser light. The connection between the laser transmitter and receiver 18 and the gas collection cabin 15 is required to be unsealed, leaving exhaust and operation holes. The movable scale 17 and the gas collection cabin 15 are sealed in a gap, so that the movable scale 17 can slide without resistance on the inner wall of the gas collection cabin 15 while being airtight. The liquid position monitoring device is used to collect liquid level changes.

Usage steps: firstly, about 100 g the substance (solid/liquid) to be tested is weighed. For the solid with large particles, it can be crushed by using appropriate tools and put into the liquid-filled flask 10, the liquid-filled flask stopper 3 is covered, and the funnel switch 2 is turned off to obtain the initial state of FIG. 4.

Then, the device switch is turned on, and the device is self-checked and preheated. The button 8 of the display screen is opened to form the state shown in FIG. 3. Through the window, you can observe the liquid level height, reaction state, stirring situation and so on. Water is added into the water adding funnel 1, the funnel switch 2 is turned on, so that the water can quickly flow down and contact with the object to be detected, and then the funnel switch 2 is turned off until the object to be detected is completely covered by the water, and the timer button is pressed.

Secondly, the reaction degree is observed, the stirring button is pressed, and the magnetic stirrer 13 will start stirring under the magnetic force to promote the reaction.

Thirdly, the laser transmitter and receiver 18 transmits and receives once every 10 s from the time when the timer button is pressed, and the moving distance of the movable scale 17 can be calculated according to the received time, the generated gas volume can be calculated according to the moving distance and the cross-sectional area of the gas collection cabin 15, and the gas release speed can be calculated according to the generated gas volume and time, so as to form a gas release speed time curve to be displayed on the display screen.

Finally, the gas sensors 16 include combustible gas, oxygen, and toxic gases such as chlorine gas, sulfur dioxide, hydrogen sulfide, etc. (multiple sensors can be configured as required). After pressing the timer button, the gas sensor 16 records readings once every 10 s, and forms a concentration-time curve to be displayed on the display screen. Data is read and recorded after 15 min of reaction time, and the volume test range is 25 ml-2000 ml. If the reaction is violent and the gas release rate exceeds L/min, the test is stopped in time and the result is recorded as category A.

The disclosure provides a portable experimental device for hazardous chemicals and an experimental method thereof, which not only improves the accuracy of fire scene experimental detection, but also enhances the efficiency of on-site emergency response, and provides strong technical support for fire site experimental detection, prevention and rescue work.

Those skilled in the art can clearly understand that the technology in the embodiment of the disclosure can be realized by means of software and necessary general hardware platform. Based on this understanding, the technical solution in the embodiment of the disclosure being essential or contributing to the prior art can be embodied in the form of a software product, which can be stored in a storage medium, such as ROM/RAM, a magnetic disk, an optical disk, etc., and includes several instructions to make a computer device (which can be a personal computer, a server, or a network device, etc.) execute the methods described in various embodiments or some parts of the embodiments of the disclosure.

The above-mentioned embodiments of the disclosure do not limit the scope of protection of the disclosure. In addition, in the description of this disclosure, "plural" means two or more than two unless otherwise specified. In addition, in order to clearly describe the technical scheme of the embodiment of the disclosure, the words "first" and "second" are used in the embodiment of the disclosure to distinguish the same or similar items with basically the same functions and functions. Those skilled in the art can understand that the words "first" and "second" are not limited to the quantity and execution order, and the words "first" and "second" are not necessarily different. The above-mentioned embodiments of the disclosure do not constitute a limitation on the protection scope of the disclosure.

The embodiments of the disclosure described above are not intended to limit the scope of protection of the disclosure.

What is claimed is:

1. A portable experimental device for hazardous chemicals, wherein the portable experimental device for hazardous chemicals comprises an experimental device main body and a control device, the control device is installed inside the experimental device main body; an outer wall of the experimental device main body is provided with a display screen and buttons; a top of the experimental device main body is provided with a through hole for installing a water adding funnel, a funnel switch and a liquid-filled flask stopper; and a liquid-filled flask, a heating insulation electric jacket, a temperature sensor and a magnetic stirrer are further installed in the experimental device main body; the water adding funnel is installed on a top of the liquid-filled flask through the funnel switch, and a gas collection cabin is further installed inside the experimental device main body, and the gas collection cabin is connected with the liquid-filled flask through a connecting hose, and the gas collection cabin is provided with gas sensors, a movable scale and a laser transmitter and receiver; an inner wall of the experimental device main body is further provided with an explosion-proof battery and a liquid position monitoring device, and the liquid position monitoring device, the explosion-proof battery, the temperature sensor and the heating insulation electric jacket are electrically connected with the control device;

the control device comprises a hazardous chemicals database construction unit, a first fire scene test experimental data analysis unit, a second fire scene test experimental data analysis unit and an information sharing unit;

the hazardous chemicals database construction unit, used for obtaining hazardous chemicals information and portable experimental device basic information for hazardous chemicals, wherein the hazardous chemicals information comprises chemical name and chemical formula information, physical property information, chemical property information and hazardous characteristic information, and the portable experimental device basic information for hazardous chemicals comprises sensor information, location information, device operation information and network information, and building a hazardous chemicals database based on obtained hazardous chemicals information and portable experimental device basic information for hazardous chemicals;

a first fire scene test experimental data analysis unit, used for receiving scene detection data collected by the portable experimental device for hazardous chemicals in a fire scene, matching the scene detection data after preprocessing with information in the hazardous chemicals database, so as to obtain a first fire scene prediction result;

a model optimization unit, used for dividing scene detection data preprocessed data into a training set and a test set, and training a random forest model by using the training set according to a relationship between hazardous chemical fire risks and characteristics, so as to obtain a fire scene chemical reaction prediction model;

the second fire scene test experimental data analysis unit, used for substituting scene detection data obtained by real-time detection of the portable experimental device for hazardous chemicals in a fire scene into the fire scene chemical reaction prediction model, so as to obtain a second fire scene prediction result;

the information sharing unit, used for comparing the first fire scene prediction result with the second fire scene prediction result, wherein if a comparison result is consistent, a fire scene test experimental result is generated, and the fire scene test experimental result is shared to mobile terminal devices at a fire scene.

2. A portable experimental method for hazardous chemicals, used in the portable experimental device for hazardous chemicals according to claim 1, comprising:

obtaining hazardous chemicals information and portable experimental device basic information for hazardous chemicals, wherein the hazardous chemicals information comprises chemical name and chemical formula information, physical property information, chemical property information and hazardous characteristic information, and the portable experimental device basic information for hazardous chemicals comprises sensor information, location information, device operation information and network information, and building a hazardous chemicals database based on obtained hazardous chemicals information and portable experimental device basic information for hazardous chemicals;

receiving scene detection data collected by the portable experimental device for hazardous chemicals in a fire scene, matching the scene detection data after preprocessing with information in the hazardous chemicals database, so as to a first fire scene prediction result;

dividing scene detection data preprocessed data into a training set and a test set, and training a random forest model by using the training set according to a relationship between hazardous chemical fire risks and characteristics, so as to obtain a fire scene chemical reaction prediction model;

substituting scene detection data obtained by real-time detection of the portable experimental device for hazardous chemicals in a fire scene into the fire scene chemical reaction prediction model, so as to obtain a second fire scene prediction result;

comparing the first fire scene prediction result with the second fire scene prediction result, wherein if a comparison result is consistent, a fire scene test experimental result is generated, and sharing the fire scene test experimental result to each mobile terminal device at a fire scene.

3. The method according to claim 2, further comprising:
comparing the first fire scene prediction result with the second fire scene prediction result, wherein if a comparison result is inconsistent, various constraint conditions of fire scene working safety environment are set, and substituting scene detection data obtained by real-time detection of the portable experimental device for hazardous chemicals in a fire scene and information in the hazardous chemicals database into a preset genetic algorithm for genetic iteration, so as to obtain a third fire scene prediction result of various constraint conditions of the fire scene working safety environment.

4. The method according to claim 2, wherein obtaining hazardous chemicals information and portable experimental device basic information for hazardous chemicals, the hazardous chemicals information comprising chemical name and chemical formula information, physical property information, chemical property information and hazardous characteristic information, and the portable experimental device basic information for hazardous chemicals comprising sensor information, location information, equipment operation information and network information, and building a hazardous chemicals database based on obtained hazardous chemicals information and portable experimental device basic information for hazardous chemicals comprises:

determining hazardous chemicals database data demand information, wherein the hazardous chemicals database data demand information comprises hazardous chemicals information, information after reaction of hazardous chemicals with water and detection data of the portable experimental device for hazardous chemicals, and building a hazardous chemicals database data table according to the hazardous chemicals database data demand information;

wherein the hazardous chemicals database data table comprises a hazardous chemical table and an experimental device table, the hazardous chemical table comprises fields such as chemical name, chemical formula, physical properties, chemical properties, hazardous characteristics, and the experimental device table comprises fields such as sensor information, location information, device operation information, network information;

using VARCHAR field for chemical symbols, and converting formula into a picture format by chemical formula and storing in a database, and building a chemical formula label for stored chemical formula;

inputting real-time generated hazardous chemicals information and experimental device information into the database, and building a field index for query on the hazardous chemicals database.

5. The method according to claim 2, wherein receiving scene detection data collected by the portable experimental device for hazardous chemicals in a fire scene, matching the scene detection data after preprocessing with information in the hazardous chemicals database to obtain a first fire scene prediction result comprises:

receiving real-time detection data collected from a fire scene by a portable experimental device for hazardous chemicals through wireless transmission or wired connection;

building a fire scene information transmission network, wherein the fire scene information transmission network comprises wireless transmission and wired connection, and the wireless transmission is preferentially used for transmitting scene detection data collected by a portable experimental device used for hazardous chemicals at a fire scene and information of each mobile terminal device at a fire scene;

applying the portable experimental device for hazardous chemicals to a fire scene, and performing test experiment on 100 g substances to be tested by the portable experimental device for hazardous chemicals, wherein substances to be tested comprise solid or liquid;

collecting a liquid level height through a liquid position monitoring device by the portable experimental device for hazardous chemicals, judging reaction state by the control device according to data collected by the liquid position monitoring device, and transmitting information to an operator mobile terminal; wherein if the liquid level height meets a preset value, the funnel switch is started to add water through the water adding funnel and water pipe switch, and the funnel switch is closed until water completely covers object to be detected and a timer is started; when a preset time is reached, the magnetic stirrer starts stirring under an action of magnetic force, and the laser transmitter and receiver emits and receives once every 10 s after starting the timer, a moving distance of the movable scale is calculated according to received time, generated gas volume is calculated according to the moving distance and a cross-sectional area of the gas collection cabin, and a gas release speed is calculated according to generated gas volume and time, formed gas release speed time curve information is displayed on the display screen, and the gas release speed time curve information is transmitted to an operator control terminal;

after the timer is started, recording data once collected by the gas sensors every 10 s, and displaying formed concentration-time curve information on the display screen, and transmitting the gas release speed time curve information to the operator control terminal; reading and recording data after 15 min of reaction time, wherein volume test range is 25 ml-2000 ml; if the gas release speed time curve information and the concentration-time curve information fluctuate abnormally, a release gas rate exceeds L/min, and test is stopped in time and result is recorded as category A;

pre-processing test experiment detection result category A, and matching pre-processed test experiment detection result category A with information in the hazardous chemicals database to obtain the first fire scene prediction result, wherein the first fire scene prediction result comprises hazardous characteristic information of test experiment detection result category A.

6. The method according to claim 5, further comprising:

deploying trained fire scene chemical reaction prediction model to fire scene information transmission network application environment;

predicting real-time detected fire scene chemical reaction by the fire scene chemical reaction prediction model, and judging expected chemical reaction at a fire scene;

generating a portable experimental information report for hazardous chemicals according to prediction results of the fire scene chemical reaction prediction model.

\* \* \* \* \*